(12) United States Patent  
Gurton

(10) Patent No.: US 6,396,058 B1
(45) Date of Patent: May 28, 2002

(54) SINGLE PARTICLE CALORIC ABSORPTION SPECTROMETER

(75) Inventor: Kristan P. Gurton, Silver Spring, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 09/349,354

(22) Filed: Jun. 24, 1999

(51) Int. Cl.$^7$ .................................................. H01J 49/00
(52) U.S. Cl. ........................ 250/292; 250/281; 250/282; 250/288
(58) Field of Search .................................. 250/281, 397, 250/423 R, 292, 288, 423 P, 251, 341.6

(56) References Cited

U.S. PATENT DOCUMENTS

| | | | | |
|---|---|---|---|---|
| 4,140,905 A | * | 2/1979 | Polanyl ........................ | 250/281 |
| 4,476,100 A | * | 10/1984 | Knize et al. ................. | 423/245 |
| 4,838,706 A | * | 6/1989 | Coey et al. ................... | 374/54 |
| 5,808,299 A | * | 9/1998 | Syage ........................... | 250/288 |
| 6,168,948 B1 | * | 1/2001 | Anderson et al. ............ | 435/287 |

OTHER PUBLICATIONS

A.K. Ray, A. Souyri, E. James Davis & Theresa M. Allen "Precision of Light Scattering Techniques for Measuring Optical Parameters of Microspheres," Applied Optics vol. 30, No. 27 Sep. 20, 1991.

S. Arnold, "A Three–Axis Spherical Void Electrodynamic Levitator Trap For Microparticle Experiments," Rev. Sci, Intrum. 62(12), Dec. 1991. American Institute of Physics.

S. Arnold & L.M. Folan, Spherical Void Electrodynamic Levitator Rev Sci. Instrum, 58(9), Sep. 1987 1987 American Institute of Physics.

* cited by examiner

*Primary Examiner*—Kiet T. Nguyen
*Assistant Examiner*—David A Vanore
(74) *Attorney, Agent, or Firm*—Mark D. Kelly; William Randolph

(57) ABSTRACT

A single particle caloric absorption spectrometer for directly measuring the absorption spectra in situ of individual aerosol type particles comprises a differential arrangement of two identical electrodynamic traps (separated by a series of pneumatic valves) capable of suspending a charged particle in free-space in a non-intrusive manner in one of the traps; a source of monochromatic radiation, e.g., a laser, which is split and directed equally through transmission windows into the traps; and, a high precision capacitance manometer capable of detecting the pressure differential between the traps. After a particle has been trapped in one of the traps and the traps have been sealed from the atmosphere and from each other by the pneumatic vales, the radiation source is turned on and is evenly split/directed into both trap volumes via an appropriate beam splitter and transmission windows. This results in identical illumination of both the target and reference trap regions. A certain fraction of energy will be absorbed by the particle resulting in its heating. The heat generated within the particle is rapidly transferred to the surrounding air resulting in a net change in pressure between the target and reference traps. This change in pressure is recorded by the capacitance manometer and is shown to be proportional to the actual absorption cross section of the particle. The wavelength of the laser is then shifted slightly and the measurement is repeated until the desired spectra are completely recorded.

28 Claims, 2 Drawing Sheets

US 6,396,058 B1

SINGLE PARTICLE CALORIC ABSORPTION SPECTROMETER

I. BACKGROUND OF THE INVENTION

A. Field of the Invention

This invention relates generally to single particle absorption spectrometry and more particularly to spectrometry in which a caloric technique is used to measure the absorption spectra for a single aerosol particle.

B. Description of the Prior Art

In this application several publications are referenced by Arabic numerals in parentheses. Full citations for these publications may be found at the end of the written description immediately preceding the claims. The disclosures of all such publications, in their entireties, are hereby expressly incorporated by reference in this application as if fully set forth, for purposes of indicating the background of the invention and illustrating the state of the art.

Recent experiences in the Gulf War and with the Sarin poisonous gas attack in a Japanese subway, have demonstrated the susceptibility of both military and civilian personal to chemical/biological aerosol attacks and the need to develop some type of early warning system. Current methods for real time biological aerosol detection attempt to exploit the relatively weak fluorescence phenomena inherent in all living materials. Unfortunately, measured fluorescent spectra are often quite broad and featureless, making species discrimination and/or identification nearly impossible. It has become apparent that additional criteria must be considered, i.e., absorption, if effective identification schemes are to be developed.

In addition, researchers have proposed sophisticated models that might be able to predict how complex aerosols such as soot (important in predicting global warming) and spore cells (the types of aerosols encountered in biological warfare) absorb electromagnetic energy at certain frequencies, but have expressed frustration in not having good experimental data to compare.(2,3,4)

At the heart of these problems is the absence of detailed absorption spectra derived directly from in situ aerosols, preferably a single particle. This lack of detailed information for certain aerosols arises from the fact that all prior scientific studies involving absorption have used a conventional photoacoustic approach in which an ensemble or distribution of aerosol particles are used in the measurement. (5,6,7) This conventional approach has one major drawback: measurements conducted on an ensemble distribution of aerosols, even those with the most narrow of size distributions, severely mask fine detailed structures inherent in the absorption spectra due to averaging effects over both size and spatial orientation of the particles.(8)

Another weak point associated with conventional methods is that it is impossible to conduct a detailed study involving specific particle morphology (e.g., the type of study one would like to conduct when considering single cell organisms) when an ensemble approach is considered. Because this apparatus/technique can derives absorption spectra from a single aerosol particle, it is uniquely suited for detection schemes that require functionality at extremely low aerosol densities. Thus, for all practical purposes, to date there have been no rapid, reliable, effective means for early detection of bioaerosols that could be used to warn populations at risk in sufficient time to take evasive measures.

II. BRIEF DESCRIPTION OF THE DRAWINGS

III. SUMMARY AND OBJECTS OF THE INVENTION

It is an object of this invention to develop a method and a device capable of:

1) producing the free-space levitation of a single aerosol type particle (via an electrodynamic trap) to permit detailed analysis and study of the absorption characteristics without the detrimental effects of ensemble averaging inherent using current techniques;

2) identification and discrimination of hazardous bioaerosols to enable rapid detection of and early warning against a variety of hazardous aerosols;

3) direct measurement of absorption spectra of individual particles in situ, thus allowing for very specific control in variation of important particle parameters, e.g., size, shape, composition, etc.

These and other objects are satisfied, at least in part, by a single particle absorption spectrometer including a first particle trap having several transmission windows; a second particle trap having several transmission windows, the second particle trap placed in contact with the first particle trap; a plurality of pneumatic valves for barometrically isolating the particle traps from each other and from the outside atmosphere; a very sensitive differential capacitance manometer for measuring the pressure difference between the two particle traps; and, a source of relatively monochromatic radiation directed in equal power through the transmission windows into the particle traps, e.g., a laser. Thus, the present invention provides an efficient, simple and effective means of suspending a single aerosol type particle stationary in free-space so that thermal changes in the particle (induced by optical absorption of the irradiating source) can be measured.

Still other objects of the present invention will become readily apparent to those skilled in this art from the following description wherein, where there is shown and described a preferred embodiment of this invention, simply by way of illustration one of the modes to best carry out the invention. As it will be realized, the invention is capable of other different embodiments and its several details are capable of modification in various, obvious aspects all without departing from the invention. Accordingly, the drawings and descriptions will be regarded as illustrative in nature and not restrictive.

IV. DETAILED DESCRIPTION OF THE PREFERRED EMBODIMENTS

Figure 1:
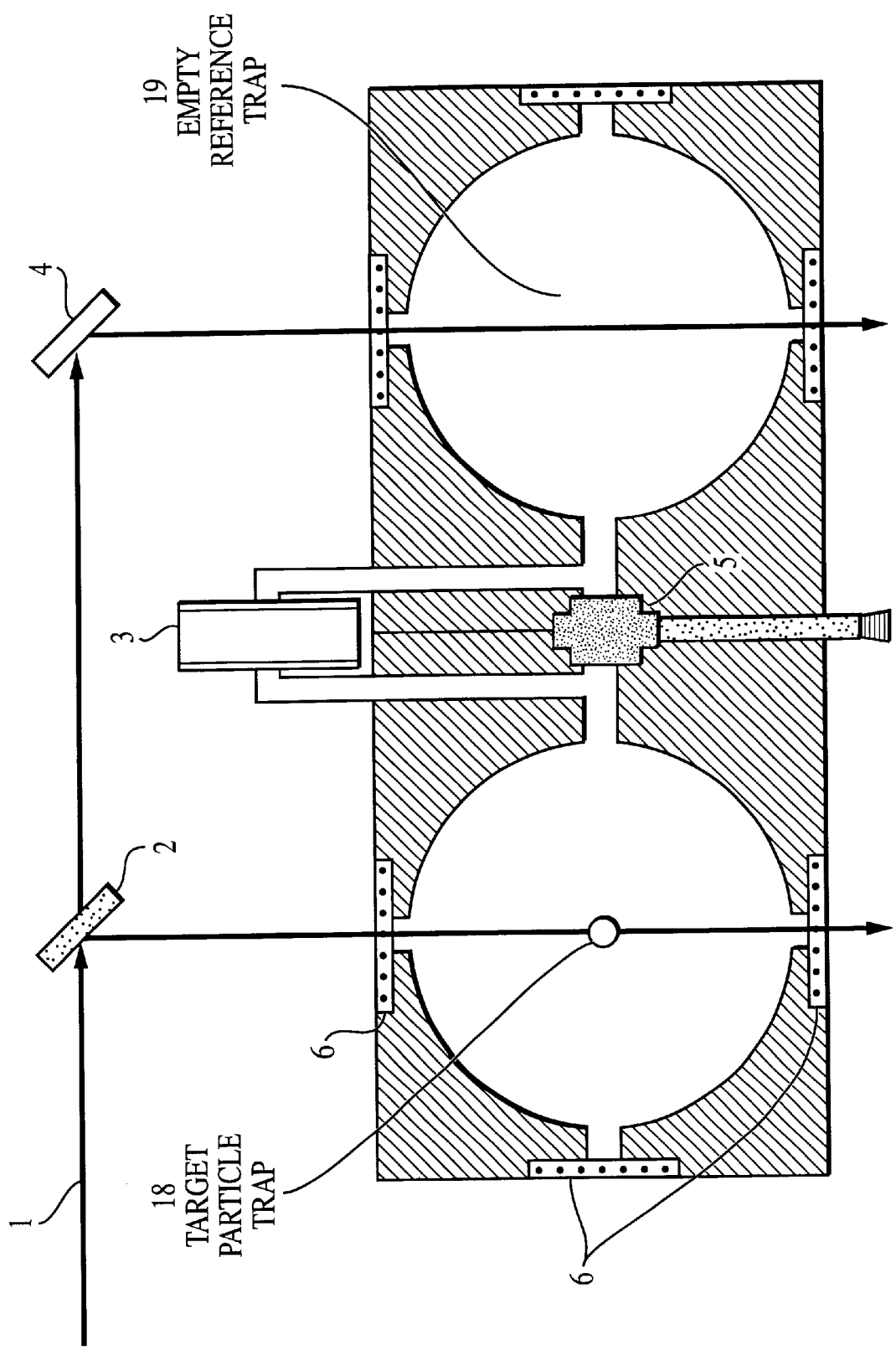
FIG. 1 shows a top cut-away view of the principal components of a preferred embodiment of the invention of this application.
Figure 2:
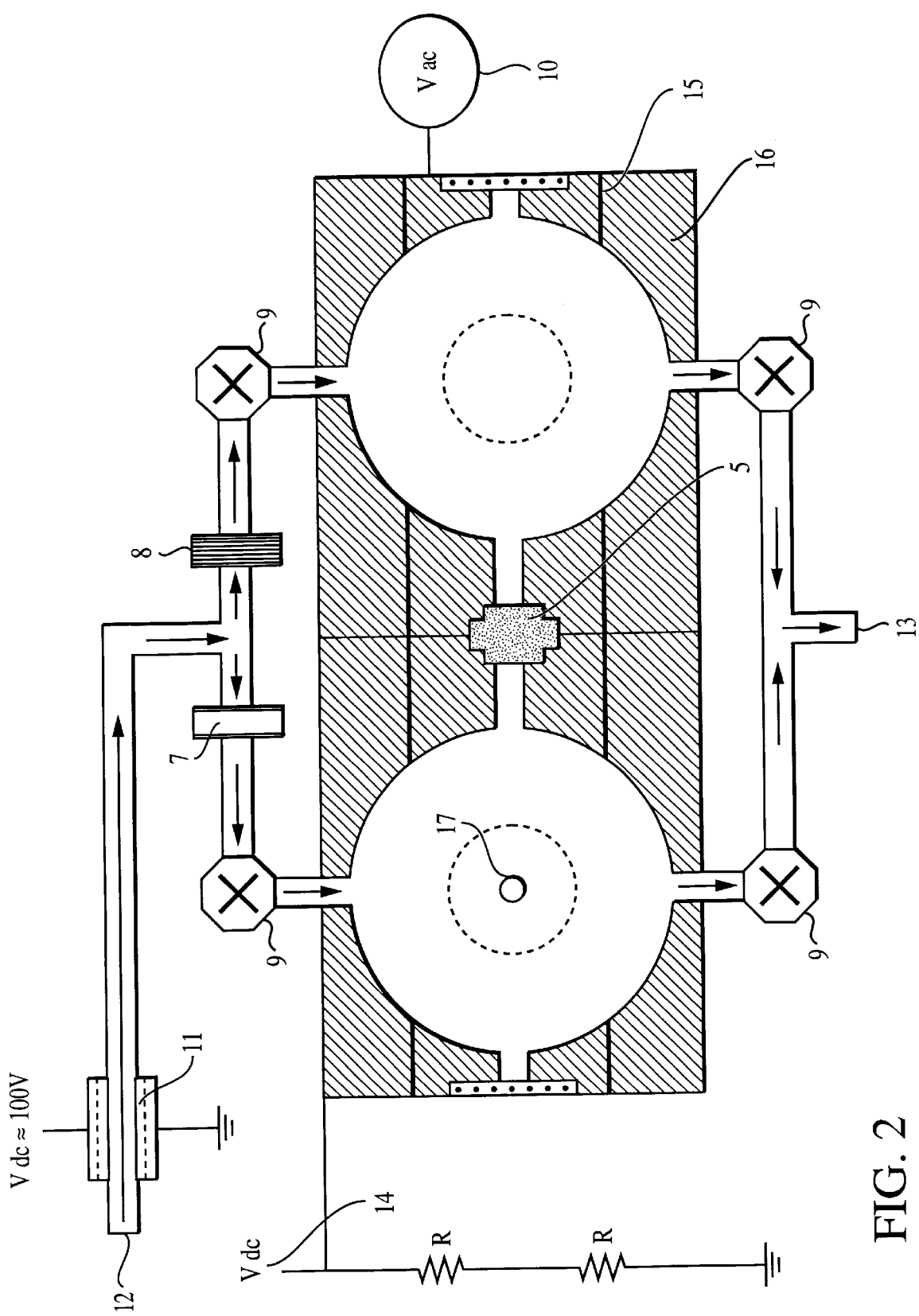
FIG. 2 shows a side cut-away view of the principal components of a preferred embodiment of the invention of this application.

As can be seen in FIGS. 1 and 2, an ensemble of individual particles are gently drawn into the aerosol input 12 through a region of high electric potential 11, thus inducing a charge on the particles. A potential of about 100 volts DC should be sufficient to induce a net charge on the particle(s). When the four pneumatic valves 9 are open, the charged aerosol flow is evenly split allowing one half of the flow to be drawn through an empty particulate filter holder 7 and into the target trap, while the other particulate volume is filtered at holder 8 which allows only ambient air to pass to the reference trap. Although a spherical void trap geometry is used here, a variety of electrodynamic trap geometries suitable for use in the present invention might also suffice, e.g., hyperbolic, ring, parallel plate, etc., and would be familiar to those of ordinary skill in the art (9,10).

A good discussion of the basic operation of particle traps is found in the book Optical Effects Associated With Small Particles, Barber, P. W., Chang, R. K., World Scientific Press, New York, 1989, incorporated herein by reference for background purposes. Basically, particles of a selected charge to mass ratio are held within a quadruple induced electric field, which contains an AC component. It is a property of such a quadruple potential that the particles are stably trapped only under certain conditions, which depend on the charge to mass ratio, the amplitude and frequency of the AC and DC potentials, and the physical dimensions of the trap.

In a preferred embodiment shown in FIGS. 1 and 2, the "balanced system" includes a differential arrangement in order to cancel spurious absorption artifacts inherent to the windows. Two identical spherical void trap volumes, target particle trap 18, and empty reference trap 19, are placed in contact to ensure that thermal equilibrium is achieved between the two trap regions. The two trap regions 18 and 19 are isolated one from the other and from the outside atmosphere when pneumatic slide valves 9 are closed simultaneously.

FIGS. 1 and 2 show a single levitated particle 17 suspended in the center of target particle trap 18. Charged particle 17 is suspended by applying both carefully controlled AC and DC voltages from AC source 10 and DC source 14, respectively, to the void's center and end-caps respectively, and thus induce the levitating electrodynamic field so that the single particle 17 becomes isolated/suspended in the exact center of the target trap. The AC voltage source 10 is approximately 100 volts. Following levitation/isolation of the test particle 17, the four valves are closed to seal off both chambers from the outside atmosphere and to pneumatically seal off the target trap from the reference trap. Both spherical voids thus contain two identical volumes of air that are in thermal equilibrium, one having the particle to be measured (the target trap), and one that is empty (the reference trap). The pressure differential between the two traps will be zero at this point. Next, monochromatic light source 22, which can be a continuous wave or a pulse, is energized and light from light source 1, is directed into 50/50 beam splitter 2. While a wavelength tunable monochromatic laser source is used in a preferred embodiment, a filtered incoherent lamp source would also work. The two beams exit beam splitter 2 at right angles, one beam is sent directly into target trap 18 (via a transmission window 6) and illuminates the particle 17, while the other half of the beam is directed into the reference trap by a turning mirror 4. This results in identical illumination of both the target and reference trap regions. It is important that the beam from slight source 1 be tightly focused on the area where the particle is suspended so that maximum power is directed at the particle 17. Connected across the two traps is a highly sensitive differential capacitance manometer 3 for measuring the pressure difference between the two trap regions. A precision molecular variable leak 5 may optionally be inserted between the two chambers in order to reduce ambient drift due to temperature inhomogeneities within the device. A certain fraction of the laser energy will be absorbed by the particle resulting in its heating. The heat generated within the particle is rapidly transferred to the surrounding air resulting in a net change in pressure between the target and reference traps. This change in pressure is recorded by the capacitance manometer 3 and is shown to be proportional to the actual absorption cross section of the particle. The high precision capacitance manometer should be capable of detecting pressure differentials on the order of 0.01 mtorr. The wavelength of the laser is then shifted slightly and the measurement is repeated until the desired spectra are completely recorded. Optionally, other particle parameters (e.g., radius, shape, and spatial orientation) can be measured by observing the scattered light (via one of the empty observation windows 6) or by real-time video imagery recorded with a high resolution CCD digital imaging camera. Both chambers should be positioned on a rigid assembly that proves good isolation from thermal and barometric fluctuations to permit accurate measurements.

The caloric technique as outlined here is highly robust and stable, and is ideally suited for deployment as a "battlefield hardened" instrument that is designed to detect and identify minute quantities of hazardous chemical and biological aerosols. The device described here may also have application within the medical research community in which detailed information is needed on how certain forms of radiation affect single cells and their constitutes.

Having thus shown and described what are at present considered to be preferred embodiments of the present invention, it should be noted that the same have been made by way of illustration and not limitation. Accordingly, all modifications, alterations and changes coming within the spirit and scope of the present invention are herein meant to be included. Many modifications of the preferred embodiments, which will still be within the spirit and scope of the invention will be apparent to those with ordinary skill in the art. In order to apprise of the various embodiments that may fall within the scope of the invention, the following claims are made.

References

1. G. W. Faris, R. A. Copeland, "Spectrally Resolved Absolute Fluorescence Cross Section of B. Globigii and B. Cereus", Stanford Research Institute, Technical Report 2913, (1992).
2. S. C. Hill, H. I. Saleheen, "Volume current method for modeling light scattering by inhomogeneously perturbed spheres", Opt. Soc. Am., 12, no.5, (1995).
3. G. Videen, D. Ngo, "Light scattering from a sphere with an irregular inclusion", Opt. Soc. Am., 12, no.5, (1995).
4. M. Iskander, H. Chen, "Optical Scattering and Absorption by Branched Chain of Aerosols", Appl. Opt., 28, no. 15, 3083, (1989).
5. C. W. Bruce, "Development of Flow Through Spectrophones for CW and Pulsed Radiation Sources", ECOM Tech. Report No. 5802, p. 1–57, (1976).
6. C. W. Bruce, K. P. Gurton, T. F. Stromberg, "Trans-Spectral Absorption and Scattering of Electromagnetic Radiation by Diesel Soot," Applied Optics, 30, No. 12, pp. 1537–1546, (1991).
7. K. P. Gurton, C. W. Bruce, "Mid-Infrared Optical Properties of Petroleum Oil Aerosols," Army Research Laboratory Technical Report, No. ARL-TR-255, White Sands Missile Range, NM. pp. 1–43, (1994).
8. A. V. Jelinek, C. W. Bruce, "Extinction Spectra of High Conductivity Fibrous Aerosols". J. Appl. Physics, 78, 2675, (1995).
9. S. Arnold, "A Three-axis spherical void electrodynamic levitator trap for microparticle experiments", Rev. Sci. Instrum., 62, 3025, (1991).
10. A. K. Ray, A. Souyri, E. J. Davis, "Precision of light scattering techniques for measuring optical parameters of microspheres", Appl. Opt. 30, no. 27, 3974, (1991).
11. J. Ho, "Real Time Detection of Biological Aerosols", Defense Research Establishment Suffleld, DRES R&D Bulletin 96001, (1996).
12. P. Hairston, J. Ho, F. R. Quant, "Design of an Instrument for Real-Time Detection of Bioaerosols using Simultaneous Measurement of Particle Aerodynamic Size and Intrinsic Fluorescence", J. Aerosol Sci. 28, no.3, 471, (1997).

I claim:

1. A single particle caloric absorption spectrometer, comprising:

a first particle trap having a transmission window;

a second particle trap having a transmission window;

conduit means connected to the first and second particle traps for selectively introducing particles into one of the first and second particle traps;

valve means connected to the conduit means for controlling the flow of particles into and out of the first and second particle traps;

a source of radiation directed through the transmission windows of the first and second particle traps; and a pressure sensor for measuring the pressure difference between the first and second particle traps.

2. The single particle caloric absorption spectrometer of claim 1, further comprising: a molecular variable leak means connected to and extending between first and second particle traps for reducing the ambient drift due to ambient temperature differences between the first and second particle traps.

3. The single particle caloric absorption spectrometer of claim 1, wherein the radiation source comprises a laser.

4. The single particle caloric absorption spectrometer of claim 3, wherein the laser is tunable at different wavelenths.

5. The single particle caloric absorption spectrometer of claim 1, further comprising a means for suspending a single particle within one of the first and second particle traps and the particle is selected from the particles introduced into the selected one of the first and second particle traps.

6. The single particle caloric absorption spectrometer of claim 5 wherein the means for suspending the single particle in the selected one of the first and second traps comprises a means for applying AC and DC electric potentials to different portions of the first and second particle traps.

7. The single particle caloric absorption spectrometer of claim 1, further comprising a charging means connected to the conduit means for inducing electrical charges on the particles passing through the conduit means.

8. The single particle caloric absorption spectrometer of claim 7, further comprising a means for suspending a single particle within one of the first and second particle traps and the particle selected from the particles introduced into the selected one of the first and second particle traps.

9. The single particle caloric absorption spectrometer of claim 8, wherein the means for suspending a particle in the selected one of the first and second traps comprises a means for applying AC and DC potentials to different portions of the first and second particle traps.

10. The single particle caloric absorption spectrometer of claim 1, wherein at least one particle trap comprises a hyperbolic electrodynamic trap.

11. The single particle caloric absorption spectrometer of claim 1, wherein the valve means comprise pneumatic valves.

12. The single particle caloric absorption spectrometer of claim 1, wherein the radiation source comprises a laser tunable at different frequencies and wherein the means for suspending a particle in the selected one of the first and second traps comprises a means for applying AC and DC potentials to different portions of the first and second particle traps.

13. The single particle caloric absorption spectrometer of claim 1, further comprising: a molecular variable leak valve connected to and extending between first and second particle traps for reducing the ambient drift due to ambient temperature differences between the first and second particle traps by controlling the pressure differences between first and second traps.

14. The single particle caloric absorption spectrometer of claim 1, wherein at least one particle trap comprises a hyperbolic electrodynamic trap and further comprising a means for suspending a particle within the hyperbolic electrodynamic by applying AC and DC electric potentials to different portions of the first and second particle traps.

15. The single particle caloric absorption spectrometer of claim 1, wherein pressure sensor comprises a differential capacitance manometer.

16. A single particle caloric absorption spectrometer, comprising:

a first particle trap having a transmission window;

a second particle trap having a transmission window;

conduit means connected to the first and second particle traps for introducing particles into the first particle trap and for preventing the flow of particles into the second particle trap;

means for suspending a selected particle within the first particle trap;

valve means connected to the conduit means for sealing the first and second particle traps;

a source of radiation directed through the transmission windows of the first and second particle traps, wherein the source of radiation irradiates the suspended particle; and a pressure sensor for measuring the pressure difference between the first and second particle traps.

17. The single particle caloric absorption spectrometer of claim 16, wherein the means for suspending a selected particle in the first particle trap comprises a means for applying AC and DC electric potentials to different portions of the first second particle trap.

18. The single particle caloric absorption spectrometer of claim 16, further comprising a charging means connected to the conduit means for inducing electrical charges on the particles passing through the conduit means.

19. The single particle caloric absorption spectrometer of claim 16, wherein the first and second particle traps comprise hyperbolic electrodynamic traps.

20. The single particle caloric absorption spectrometer of claim 16, wherein the radiation source comprises a laser tunable at different frequencies and wherein the means for suspending a particle in the selected one of the first and second traps comprises a means for applying AC and DC potentials to different portions of the first and second particle traps.

21. The single particle caloric absorption spectrometer of claim 16, further comprising: a molecular variable leak valve connected to and extending between first and second particle traps for reducing the ambient drift due to ambient temperature differences between the first and second particle traps by controlling the pressure differences between them.

22. The single particle caloric absorption spectrometer of claim 16, wherein pressure sensor comprises a differential capacitance manometer.

23. The single particle caloric absorption spectrometer of claim 16, wherein the radiation source comprises a laser and wherein a beam splitter means is used to direct the laser light beam produced therefrom through the transmission windows of the first and second particle traps.

24. A method of caloric spectrometry, comprising the steps of:

charging at least one particle;

introducing the particles into one of a first or a second chamber so that one of the chambers remains empty of the particles;

trapping and isolating a single particle from the particles in the one of the first or second chambers;

irradiating the isolated particle in the one of the first or second chambers and irradiating the one of the chambers that remains empty of the particles with a source of electromagnetic radiation; and measuring the pressure differences between the first and second chambers.

25. The method of claim 24, further comprising the step of re-measuring the pressure difference between the two chambers after changing the frequency of the radiation emitted from the electromagnetic radiation source.

26. In a device having particle traps, a method of caloric spectrometry, comprising the steps of:

placing an electrical charge on a plurality of particles;

introducing the particles into a first particle trap;

trapping and isolating a single particle from the particles in the first particle trap;

sealing the particle traps;

radiating the isolated particle in the first particle trap and the other particle traps; and measuring the pressure differences between the particle traps.

27. The method of claim 26, further comprising the step of re-measuring the pressure difference between the two chambers after changing the frequency of the radiation emitted from the electromagnetic radiation source.

28. The method of claim 26, further comprising the step of after introducing the particles into the particle trap of adjusting the ambient pressure drift between the particle traps due to ambient temperature differences by controlling the pressure differences between the particle traps.

* * * * *